United States Patent
Fridman et al.

(10) Patent No.: US 9,725,380 B2
(45) Date of Patent: Aug. 8, 2017

(54) DEHYDROGENATION PROCESS WITH HEAT GENERATING MATERIAL

(71) Applicant: CLARIANT CORPORATION, Louisville, KY (US)

(72) Inventors: Vladimir Fridman, Louisville, KY (US); Michael A. Urbancic, Louisville, KY (US)

(73) Assignee: Clariant Corporation, Louisville, KY (US)

( * ) Notice: Subject to any disclaimer, the term of this patent is extended or adjusted under 35 U.S.C. 154(b) by 367 days.

(21) Appl. No.: 14/210,610

(22) Filed: Mar. 14, 2014

(65) Prior Publication Data
US 2015/0259265 A1    Sep. 17, 2015

(51) Int. Cl.
| | |
|---|---|
| C07C 5/333 | (2006.01) |
| C07C 5/327 | (2006.01) |
| C07C 5/32 | (2006.01) |
| B01J 37/04 | (2006.01) |
| B01J 37/18 | (2006.01) |
| B01J 23/889 | (2006.01) |
| B01J 35/00 | (2006.01) |
| B01J 23/00 | (2006.01) |
| B01J 23/26 | (2006.01) |
| B01J 35/02 | (2006.01) |
| B01J 37/02 | (2006.01) |
| B01J 37/03 | (2006.01) |
| B01J 38/12 | (2006.01) |
| B01J 23/92 | (2006.01) |

(52) U.S. Cl.
CPC ........... *C07C 5/3332* (2013.01); *B01J 23/002* (2013.01); *B01J 23/26* (2013.01); *B01J 23/8892* (2013.01); *B01J 23/92* (2013.01); *B01J 35/0006* (2013.01); *B01J 35/023* (2013.01); *B01J 37/0201* (2013.01); *B01J 37/03* (2013.01); *B01J 37/04* (2013.01); *B01J 37/18* (2013.01); *B01J 38/12* (2013.01); *B01J 2523/00* (2013.01); *C07C 2521/04* (2013.01); *C07C 2523/04* (2013.01); *C07C 2523/26* (2013.01); *C07C 2523/72* (2013.01); *C07C 2523/86* (2013.01); *Y02P 20/52* (2015.11); *Y02P 20/584* (2015.11)

(58) Field of Classification Search
CPC ............................. C07C 5/3332; C07C 5/333
See application file for complete search history.

(56) References Cited

U.S. PATENT DOCUMENTS

| | | | |
|---|---|---|---|
| 2,399,678 A | 5/1946 | Houdry | |
| 2,419,997 A * | 5/1947 | Houdry | C07C 5/322 502/320 |

(Continued)

FOREIGN PATENT DOCUMENTS

| | | |
|---|---|---|
| JP | 1086944 | 2/1986 |
| RU | 2157279 | 10/2000 |
| RU | 2254162 | 6/2005 |
| WO | 02068119 | 9/2002 |
| WO | 2013162014 | 10/2013 |

*Primary Examiner* — In Suk Bullock
*Assistant Examiner* — Youngsul Jeong

(57) ABSTRACT

The disclosure provides an improved endothermic hydrocarbon conversion process that comprises reacting a hydrocarbon with a multi-component catalyst bed, and regenerating the catalyst bed with air, where the air used in regeneration step and hydrocarbon are at low air to hydrocarbon ratios and optionally at near-atmospheric pressures.

19 Claims, 1 Drawing Sheet

(56) References Cited

U.S. PATENT DOCUMENTS

| | | |
|---|---|---|
| 2,423,029 A | 6/1947 | Houdry |
| 2,423,835 A | 7/1947 | Houdry |
| 3,488,402 A | 1/1970 | Michaels |
| 3,665,049 A | 5/1972 | Cornelius |
| 3,754,051 A | 8/1973 | Suzukawa |
| 3,798,178 A | 3/1974 | Soderquist |
| 3,905,917 A | 9/1975 | Nishino |
| 4,065,406 A | 12/1977 | Nishino |
| 4,149,996 A | 4/1979 | Manning |
| 4,418,237 A | 11/1983 | Imai |
| 4,435,607 A | 3/1984 | Imai |
| 4,746,643 A | 5/1988 | Buonomo |
| 4,788,371 A | 11/1988 | Imai |
| 5,108,973 A | 4/1992 | Satek |
| 5,510,557 A | 4/1996 | Gartside |
| 5,545,787 A | 8/1996 | Cooper |
| 5,827,496 A | 10/1998 | Lyon |
| 6,326,523 B1 | 12/2001 | Stahl |
| 6,891,138 B2 | 5/2005 | Dalton |
| 7,067,455 B2 | 6/2006 | Chen |
| 7,074,977 B2 | 7/2006 | Rapier |
| 7,192,987 B2 | 3/2007 | Van Egmond |
| 7,196,239 B2 | 3/2007 | Van Egmond |
| 7,199,276 B2 | 4/2007 | Sher |
| 7,622,623 B2 | 11/2009 | Fridman |
| 7,973,207 B2 * | 7/2011 | Fridman ............... B01J 23/26 502/106 |
| 2002/0183571 A1 | 12/2002 | Williams |
| 2004/0092391 A1 | 5/2004 | Rokicki |

* cited by examiner

DEHYDROGENATION PROCESS WITH HEAT GENERATING MATERIAL

BACKGROUND OF THE INVENTION

Field of the Invention

The disclosure provides an improved endothermic hydrocarbon conversion process that comprises reacting a hydrocarbon with a multi-component catalyst bed, and regenerating the catalyst bed with air, where air flows used in the regeneration step compared to hydrocarbon flows are at relatively low air to hydrocarbon ratios and dehydrogenation can be operated at or near-atmospheric pressures.

Description of Related Art

Several endothermic hydrocarbon conversion processes are utilized in commercial operations. These processes include the Houdry cyclic fixed bed dehydrogenation process, the fluid bed paraffin dehydrogenation process, the fluid bed ethylbenzene dehydrogenation process, and fluid bed catalytic cracking process, among others. Because these processes are endothermic, heat must be consumed from the surroundings in order for the hydrocarbon conversion reaction to occur. In each of these processes, at least one reaction is promoted by contacting a hydrocarbon feed with a catalyst. Further, in each of these processes there is at least one reducing and/or oxidizing reaction that regenerates the catalyst. The heat needed for the endothermic reactions to occur is typically provided in part by combustion of coke and other undesirable side products that deposit on the catalyst during the conversion process. This combustion takes place during the regeneration process. Additional heat, however, is normally needed and is usually provided by hot air or steam that is fed into the catalyst bed from external sources between the hydrocarbon conversion cycles.

In a typical Houdry dehydrogenation process (e.g., the CATOFIN® process), an aliphatic hydrocarbon (e.g., propane) passes through a dehydrogenation catalyst bed and is dehydrogenated to a complementary olefin (e.g., propylene). The olefin is then flushed from the catalyst bed, the catalyst is regenerated and reduced, and the cycle is repeated.

This process can be run as an adiabatic, cyclic process. Each cycle includes a catalyst reduction step and a dehydrogenation step, and typically further includes a step to purge the remaining hydrocarbon from the reactor, and finally a regeneration step with air. Following this, the cycle begins again with the catalyst reduction step.

This dehydrogenation reaction is highly endothermic. Therefore, during the dehydrogenation step, the temperature near the inlet of the catalyst bed (where the aliphatic hydrocarbon initially enters the catalyst bed) can decrease by as much as 100° C. This decrease in temperature causes a decrease in hydrocarbon conversion. In addition, during the dehydrogenation step, it is common for coke to form and deposit on the catalyst, further reducing the activity of the catalyst.

In order to reheat the catalyst bed and remove coke that has deposited on the catalyst during the dehydrogenation step, the reactor is typically purged of hydrocarbon and then undergoes a regeneration step with air heated to temperatures of up to 700° C. Heat is provided to the bed by the hot air that passes through the bed and also by the combustion of the coke deposits on the catalyst. Reduction of the catalyst, with a reducing gas such as hydrogen, prior to dehydrogenation step also provides some additional heat.

During regeneration, the hot air flows from the top of the catalyst bed to the bottom, and the regeneration cycle is relatively short, so there is a tendency for the top of the bed to be hotter than the bottom of the bed. The lower temperature in the bottom of the bed does not allow full utilization of the catalyst and thus the yield is lower that what would be otherwise expected. Also, the coke distribution in the catalyst bed, which is not easily controlled, affects the amount of heat added at each location and the resulting catalyst bed temperature profile. These factors make control of the temperature profile in the bed difficult.

In the conventional HOUDRY CATOFIN® process, the reactor contains a physical mixture of a chromia/alumina catalyst and an inert component. The volume ratio between the inert component and the catalyst depends on a number of factors including the type of hydrocarbon feed being used in the dehydrogenation process. For example, for a propane feed the inert component can be equal to about 50% of the total catalyst volume, whereas for an isobutane feed the volume of the inert component can be as low as about 30% of the total catalyst bed volume.

The inert component is typically a granular, alpha-alumina material of similar particle size to the catalyst that is catalytically inactive with respect to dehydrogenation or side reactions such as cracking or coking, but that has a high density and high heat capacity, so it can be used to store additional heat in the bed. The additional heat is then used during the dehydrogenation step. However, the inert component is not capable of producing heat during any stage of the process.

Houdry catalyst bed temperatures may be controlled within a temperature range suitable for the reactions without requiring an extraneous heating or cooling fluid to be circulated through or around the reaction chamber by including within the catalyst bed an inert component capable of absorbing or storing up heat which can subsequently be released as desired or required. In commercial practice for fixed bed reactors, this is typically achieved by using a physical mixture of a dehydrogenation catalyst and a granular, alpha-alumina as the catalyst bed. Although the addition of the inert component provides a reversible heat sink for the process, and helps stabilize the overall temperature swings in the reactor, the inert component is not capable of providing extra heat for the process nor can it produce heat during any stage of the process. Hence, an external heat source is still required even with the combined use of the catalyst and the inert component.

Additional aspects of the technical background are described in U.S. Pat. Nos. 7,622,623 and 7,973,207, each of which is hereby incorporated by reference herein in its entirety.

SUMMARY OF THE INVENTION

Improving endothermic hydrocarbon conversion processes to require less energy and improve heat addition but, at the same time, provide good conversion yields, still presents a challenge. It is particularly important to improve processes employed commercially. The current endothermic hydrocarbon conversion processes require air flow, but the energy costs are considerable due to the employed high air temperatures and flow rates. In certain aspects, the present invention improves the current endothermic hydrocarbon conversion processes by reacting a hydrocarbon feedstock with a multi-component catalyst bed at relatively low air to hydrocarbon ratios and/or atmospheric pressures. The processes of the disclosure can advantageously decrease the operating and capital costs while maintaining or improving hydrocarbon conversion yields and/or selectivity.

In a broad aspect, the disclosure provides processes for endothermic conversion of hydrocarbons comprising:

a) providing a reactor having a catalyst bed, the catalyst bed having an inlet section, a middle section and optionally an outlet section, wherein the inlet section of the catalyst bed has a first catalyst composition disposed therein, the first catalyst composition comprising a catalytic component, optionally physically mixed with an inert component, the middle section of the catalyst bed has a second catalyst composition disposed therein, the second catalyst composition comprising a catalytic component physically mixed with a heat-generating component and optionally an inert component, and the outlet section of the catalyst bed having a third catalyst composition disposed therein, the third catalyst composition comprising a catalytic component optionally physically mixed with an inert component, wherein the middle section of the catalyst bed is in thermal communication with the inlet section of the catalyst bed and, if present, the outlet section of the catalyst bed;

b) reducing the catalyst bed wherein the heat-generating component of the second catalytic composition generates heat that passes into the first catalyst composition (e.g., into an inert component thereof) and, if present, the third catalytic composition (e.g., into an inert component thereof); and then c) contacting a hydrocarbon feedstock with the catalyst bed to endothermically convert it to an endothermic reaction product (for example, to dehydrogenate it to a dehydrogenated hydrocarbon); and then d) optionally, purging the catalyst bed (for example, with steam); and e) regenerating the catalyst bed by contacting the catalyst bed with air, wherein (i) the air in the regeneration step and the hydrocarbon feedstock are at a ratio of between about 6.5 wt/wt and about 2 wt/wt; and optionally (ii) the contacting of the hydrocarbon feedstock with the catalyst bed is at a pressure in the range of about 0.7 to about 1.5 atmospheres.

DETAILED DESCRIPTION OF THE INVENTION

Figure 1:
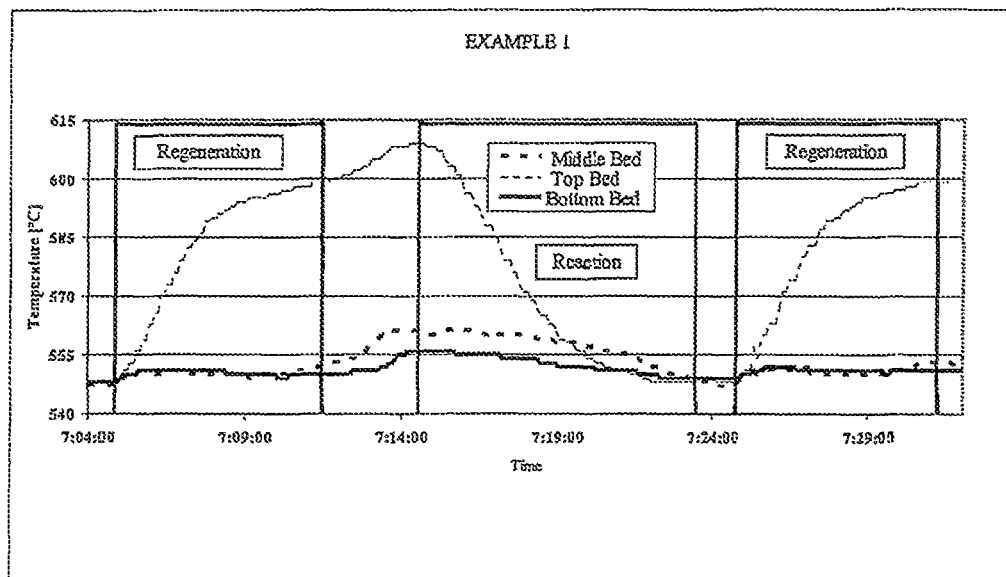
FIGS. 1 and 2 are graphs of catalyst bed temperatures for Houdry dehydrogenation processes disclosed with respect to Examples O and P, respectively.

Before the disclosed methods and materials are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein the term "contacting" includes the physical contact of at least one substance to another substance.

In view of the present disclosure, the processes described herein can be configured by the person of ordinary skill in the art to meet the desired need. In general, the disclosed processes and materials provide improvements in an endothermic hydrocarbon conversion process. For example, in certain aspects, the processes of the disclosure operate at lower air to hydrocarbon ratios while maintaining the same or higher dehydrogenated hydrocarbon yields and lower production cost. In certain aspects, the processes of the disclosure are operated near atmospheric pressures, which can also lead to lower production cost.

The processes of the disclosure require that a hydrocarbon feedstock contacts a multi-component catalyst bed in order to effect an endothermic hydrocarbon conversion (for example, a dehydrogenation, e.g., of aliphatic hydrocarbon to olefin). In certain embodiments, the catalyst bed has an inlet section, a middle section and optionally an outlet section, wherein:

the inlet section of the catalyst bed has a first catalyst composition disposed therein, the first catalyst composition comprising a catalytic component optionally physically mixed with an inert component, the middle section of the catalyst bed has a second catalyst composition disposed therein, the second catalyst composition comprising a catalytic component physically mixed with a heat-generating component (and, optionally, an inert component), and the outlet section of the catalyst bed, if present, having a third catalyst composition disposed therein, the third catalyst composition comprising a catalytic component optionally physically mixed with an inert component, wherein the middle section of the catalyst bed is in thermal communication with the inlet section of the catalyst bed and, if present, with the outlet section of the catalyst bed. In certain such embodiments, the outlet section of the catalyst bed is present.

The catalytic component used in each catalyst composition is a catalyst that is effective to convert the hydrocarbon feed to a predetermined product or product mix via an endothermic reaction, e.g., the dehydrogenation of the hydrocarbon feed to form a dehydrogenated hydrocarbon, e.g., an olefin. The heat-generating component is a material that generates heat upon being exposed to reducing and/or to oxidizing reaction conditions but is relatively (e.g., substantially) inert to the hydrocarbon feedstock with respect to undesirable side reactions, such as coke formation. Optionally, the heat-generating component may catalyze the conversion of the hydrocarbon to the desired product or product mix.

For the purposes of describing the invention in detail, improvements to the Houdry cyclic dehydrogenation process using a fixed bed reactor will be used as an embodiment. It is to be understood, however, that the processes described herein may be modified without deviating from the scope of the disclosure to function in the inventive manner in other cyclic, endothermic hydrocarbon conversion processes.

For the purposes of describing the invention, but without intending any limitation through such description, the fixed catalyst bed is essentially divided into three parts—the inlet section of bed, a middle section of bed, the outlet section of bed. As the names indicate, the inlet section is the section (of the three) closest (with respect to fluid flow in the reactor) to the inlet and the outlet section is the section (of the three) closest to the outlet of the reactor. As the person of ordinary skill in the art will appreciate, the inlet section need not actually encompass the inlet of the reactor, although in certain embodiments it does. Similarly, the outlet section need not actually encompass the outlet of the reactor, although in certain embodiments it does. The middle section of the bed is disposed between the inlet section and the outlet section (with respect to fluid flow in the reactor), in thermal communication with each. The middle section can be disposed, for example, immediately between the inlet section and the outlet section, with no intervening sections of the catalyst bed. In certain embodiments, the inlet section is disposed under the middle section, which is disposed under the outlet section (e.g., as layers at the bottom of a reactor volume). For example, as the person of ordinary skill in the art will appreciate, the three sections of the catalyst bed may be defined by layers of catalytic compositions As described above, for each of the inlet and outlet sections of the bed, a catalytic component is combined with an inert component for use in the inlet and outlet sections of the bed; and the catalytic component combined with the heat-generating component, optionally with an inert component, is used in the middle section of the bed. While convenient for description purposes, it should be understood that several variations in the component combinations are possible with the fixed catalyst bed. For example, when the bed is divided into three sections, the bed may be divided such that (a) each of the three sections is of approximately equal volume, or (b) the middle section may be larger than about one-third the total catalyst volume, or (c) the middle section may be smaller than about one-third the total catalyst volume, or (d) the inlet section and the outlet section may be of unequal volumes, or (e) any combination thereof. Of course, in other embodiments, the three parts of the bed are of different sizes. In certain embodiments, the inlet section may be present at a volume within the range of about 1 vol % to about 65 vol % of the total volume of the catalyst bed. Similarly, the outlet section may be present at a volume within the range of from 0 vol % to about 65 vol % of the total volume of the catalyst bed. The middle section of the bed may be present at a volume within the range of about 5 vol % to about 80 vol % of the total volume of the catalyst bed. In certain specific embodiments, the inlet section of the bed is present at a volume within the range of about 20 vol % to about 50 vol % of the total volume of the catalyst bed and the middle section of the bed is present at a volume within the range of about 20 vol % to about 80 vol % of the total volume of the catalyst bed. In other specific embodiments, the inlet section of the bed is present at a volume within the range of about 5 vol % to about 50 vol % of the total volume of the catalyst bed, the middle section of the bed is present at a volume within the range of about 30 vol % to about 80 vol % of the total volume of the catalyst bed, and the outlet section is present at a volume within the range of from 0 vol % to about 50 vol % of the total volume of the catalyst bed.

As the person of ordinary skill in the art will appreciate, the same catalytic component can be used in the first, second and third catalytic compositions. In other embodiments, different catalytic components can be used. For example, different catalytic components can be used in all three of the catalytic compositions. Alternatively, the same catalytic component can be used in the first and second; the first and third; or the second and third catalytic compositions and a different catalytic component can be used in the other catalytic composition.

Similarly, the same inert component can be used in the first, second (if present) and third catalytic compositions. In other embodiments, different inert components can be used. For example, different inert components can be used in all three of the catalytic compositions. Alternatively, the same inert component can be used in the first and second; the first and third; or the second and third catalytic compositions and a different inert component can be used in the other catalytic composition.

In certain embodiments, the first catalytic composition is substantially the same as the third catalytic composition, e.g., and the second catalytic composition is substantially different than the first catalytic composition and the third catalytic composition.

In each of the catalytic compositions, the catalytic component and may be any catalyst suitable for use in dehydrogenation reactions, such as a Catofin® catalyst available from Clariant Corporation, Charlotte, N.C. For example, Catofin® 300 catalyst is a chromium oxide dehydrogenation catalyst, manufactured on an alumina support, comprising from about 17 wt % to about 22 wt % $Cr_2O_3$.

In other embodiments, the catalytic component comprises, disposed on an alumina support, chromium oxide (e.g., $Cr_2O_3$) in an amount in the range of about 15 to about 25 wt %, and, optionally, potassium oxide in an amount up to about 5 wt %. In still other embodiments, the catalytic component is any catalyst described in U.S. Pat. No. 5,108,973 or in International Patent Application Publication no. 02/068119, each of which is hereby incorporated herein by reference in its entirety.

Of course, other catalytic components can be used, as would be evident to the person of ordinary skill in the art. As is known in the art, a catalytic component generally has one or more active components dispersed on or compounded with a carrier or support. The support provides a means for increasing the surface area of the catalyst. Several compositions for dehydrogenation catalysts have been taught in the prior art, such as the catalyst taught in U.S. Pat. No. 3,488,402 (issued to Michaels et al., and incorporated herein by reference). The '402 catalyst comprises "alumina, magnesia, or a combination thereof, promoted with up to about 40% of an oxide of a metal" of Group 4, Group 5 or Group 6. (The terms "Group 4", "Group 5" and "Group 6" refer to the new IUPAC format numbers for the Periodic Table of the Elements. Alternative terminology, known in the art, includes the old IUPAC labels "Group IVA," "Group VA" and "Group VI-A", respectively, and the Chemical Abstract Services version of numbering as "Group IVB," "Group VB" and "Group VI-B", respectively.) Recommended carriers for dehydrogenation catalysts include aluminum oxide, aluminas, alumina monohydrate, alumina trihydrate, alumina-silica, transition aluminas, alpha-alumina, silica, silicate, aluminates, calcined hydrotalcites, zeolites and combinations thereof. For the present application, the catalyst may be prepared by any standard method known in the art, such as taught in U.S. Patent Application Publication no. 20040092391, incorporated herein in its entirety by reference.

As used herein, the heat-generating component is a material that can generate heat upon exposure to reducing reaction conditions, but is substantially inert with respect to hydrocarbon conversion to undesirable products or to undesirable side reactions. In certain embodiments, the heat-generating component comprises a metal selected from the group consisting of copper, chromium, molybdenum, vanadium, cerium, yttrium, scandium, tungsten, manganese, iron, cobalt, nickel, silver, bismuth and combinations thereof. One of skill in the art will recognize that the heat-generating component may be present in metal form or in a low valence metal oxide form, depending on the element applied after reduction. Generally, after the regeneration step, the heat-generating component may be present in a metal oxide form. Exemplary carriers for the heat-generating component include, but are not limited to, various aluminum oxides or hydroxides such as aluminum trihydroxide, boehmite, pseudo-boehmite, gibbsite, bayerite, transition aluminas or alpha-alumina, silica/alumina, silica, silicates, aluminates such as calcium aluminate or barium hexaluminate, calcined hydrotalcites, zeolites, zinc oxide, chromium oxides, magnesium oxides and combinations thereof. Optionally, the heat-generating component may further comprise a promoter, such as an alkali, an alkaline earth metal, lithium, sodium, potassium, rubidium, cesium, beryllium, magnesium, calcium, strontium, zirconium, barium and a combination thereof (i.e., in an oxidized state, e.g., in oxide form).

The metal comprises from about 1 wt % to about 100 wt % of the total heat-generating component. In one embodiment, the metal comprises from about 2 wt % to about 40 wt % of the total heat-generating component. In another embodiment, the amount of metal is from about 5 wt % to about 10 wt % of the total heat-generating component.

For example, in certain embodiments, the heat generating component includes, disposed on a carrier, copper oxide (e.g., CuO) in an amount in the range of about 3 wt % to about 20 wt % (e.g., about 5 to about 15 wt %); optionally, manganese oxide (e.g., $MnO_2$) in an amount up to about 5 wt % (e.g., up to about 2 wt %). The carrier can be, for example, alumina (e.g., alpha-alumina or gamma-alumina), calcium aluminate, boehmite alumina, or a mixture of calcium oxide and boehmite alumina.

The amount of heat-generating component added to the catalyst bed at any particular area should be determined by the amount of heat that must be replaced in the process throughout the catalyst bed. The heat generated by the heat-generating component may be, for example, less than the heat consumed by the principal reaction in each part of the catalyst bed. In certain desirable embodiments, the sum of the heat generated by the heat-generating component in the reduction and the heat generated during regeneration is less than the heat consumed by the reduction of the hydrocarbon feedstock. The person of ordinary skill in the art will determine the desired amount of heat generating component through routine experimentation, for example, using thermodynamic calculation, reactor simulation, and test reactions. The heat-generating component is preferably present in the middle section of the catalyst bed in an amount that is at least about 10% of the total mass of the catalyst bed therein. For example, the amount of the heat-generating component in the middle section of the catalyst bed can be in the range of about 10 wt % to about 60 wt %, about 20 wt % to about 70 wt %, or about 30 wt % to about 60 wt %.

The heat-generating component can be prepared by essentially the same methods known in the art for preparing a supported catalyst. For example, the heat-generating component may be prepared by precipitation of the carrier with the metal, or by impregnation of the second carrier with the metal. Promoters may further be added with the metal, or may be otherwise added to the second component via methods known in the art for the addition of promoters. Representative preparations of heat-generating components are described below.

In certain embodiments, the heat-generating component is substantially inactive to catalyze the endothermic conversion (e.g., the dehydrogenation) of the hydrocarbon feedstock (e.g., less than about 20% or even less than about 10% of the catalytic activity of the catalytic component). In certain embodiments (e.g., when the catalyst component includes chromium oxide), the heat-generating component is substantially free of chromium.

Before loading into the reactor the catalytic component may be physically mixed with an inert component, as is known in the art. This inert component may be any material, or combination of materials, that is catalytically inactive with respect to the endothermic conversion reaction and any undesirable side reactions, but that is not capable of producing heat during any stage of the process. Desirably, the inert component has a high density and high heat capacity. A commonly used inert component is agranular, alpha-alumina material of similar particle size to the supported catalytic first component. Further, as is known in the art, the volume ratio between the inert component and the catalytic component depends on a number of factors including, but not limited to, the type of hydrocarbon feed being used in the endothermic conversion process. The person of ordinary skill in the art can, in view of the processes described herein, adjust the volume ratio between the inert component and the catalytic component. For example, the volume ratio of the inert component to the catalytic component can be in the rage of about 3:1 to about 1:3, e.g., or in the range of about 2:1 to about 1:2.

Of course, in other embodiments, the first catalytic composition and/or the third catalytic composition (if present) do not include an inert component.

The improved process of the present disclosure is intended for use in any cyclic, endothermic hydrocarbon conversion process (e.g., dehydrogenation) in a fixed bed application. The various catalytic compositions can be prepared by physically mixing the catalytic component with the inert material and/or the heat-generating component. Initially, the desired amount of catalytic component and the desired bed configuration is defined. The catalytic component is then divided into the defined quantities and is physically mixed with either the heat-generating component or with the inert material or with a combination of the heat-generating component and the inert material. The mixtures are then loaded into the reactor per the desired bed configuration (e.g., in layers).

The processes of the disclosure generally follow the typical Houdry dehydrogenation process, for example as described in U.S. Pat. No. 2,419,997, which is hereby incorporated herein by reference in its entirety. Additional aspects of the process are described in U.S. Pat. Nos. 7,622,623 and 7,973,207, each of which is hereby incorporated by reference herein in its entirety.

In one embodiment, a process of the disclosure as described herein comprises:
a) providing a reactor having a catalyst bed as described above;

b) reducing the catalyst bed such that the heat-generating component of the second catalytic composition generates heat which passes into the first catalyst composition (e.g., into an inert component thereof) and the third catalytic composition (e.g., into an inert component thereof); and
c) contacting a hydrocarbon feedstock with the catalyst bed to form a dehydrogenated hydrocarbon;
d) optionally, purging the catalyst bed (e.g., with steam); and
e) regenerating the catalyst bed by contacting the catalyst bed with air, wherein the ratio of air in the regeneration step to total hydrocarbon feedstock is in the range of about 6.5 wt/wt to about 2 wt/wt.

In another embodiment, a process of the disclosure as described herein comprises:
a) providing a reactor having a catalyst bed as described above;
b) reducing the catalyst bed such that the heat-generating component of the second catalytic composition generates heat which passes into the first catalyst composition (e.g., into an inert component thereof) and, if present, the third catalytic composition (e.g., into an inert component thereof); and
c) contacting a hydrocarbon feedstock with the catalyst bed to form a dehydrogenated hydrocarbon, and wherein the contacting of the hydrocarbon feedstock with the catalyst bed is at a pressure in the range of about 0.1 to about 1.5 atmospheres. This embodiment may further comprise:
d) optionally, purging the catalyst bed (e.g., with steam); and
e) regenerating the catalyst bed by contacting the catalyst bed with air, wherein the ratio of air in the regeneration step to total hydrocarbon is in the range of about 6.5 wt/wt to about 2 wt/wt.

In the processes as described herein, the reduction step can perform two functions. First, the reduction can reduce the catalytic component to put it in condition to dehydrogenate the hydrocarbon. Second, and critically, the reduction can cause the heat-generating component of the second catalytic composition to generate heat, which passes into the first catalyst composition (e.g., into the inert component thereof) and the third catalytic composition (e.g., into the inert component thereof), thereby heating them. (Of course, as the person or ordinary skill in the art will appreciate, the generated heat will also heat up the second catalytic composition.) For example, in certain embodiments, the reduction step increases the temperature of the first catalyst and, if present, the third catalytic composition by at least about 5° C., at least about 10° C., at least about 15° C., at least about 20° C., at least about 25° C., or even at least about 30° C. In certain embodiments, the reduction step increases the temperature of the second catalyst composition by at least about 5° C., at least about 10° C., at least about 15° C., at least about 20° C., at least about 25° C., or even at least about 30° C. In certain such embodiments, the temperature increases are up to about 150° C., up to about 100° C., or up to about 50° C. The reduction can be performed, for example, with hydrogen.

After the reduction, the hydrocarbon feedstock is contacted with the catalyst bed, thereby dehydrogenating it. Because the catalytic bed has been essentially pre-heated by the heat-generating component, the catalytic component demonstrates improved conversion relative to a reactor bed that does not include the heat-generating component. In a preferred embodiment, the heat-generating component is selected such that no significant negative effect on selectivity for the hydrocarbon conversion reaction is observed.

As the person of ordinary skill in the art will appreciate, after each hydrocarbon cycle, the catalyst bed can be purged to remove reaction products and unreacted hydrocarbon therefrom. The catalyst bed can be purged, for example, using steam. The person of ordinary skill in the art will appreciate that after regeneration conventional purge techniques can be used to prepare the catalyst bed for reduction at the beginning of each cycle.

After the endothermic conversion (and after any purging step), the catalyst bed is regenerated, for example, by oxidation with hot air (e.g., in the range of about 600° C. to about 800° C., for example, about 720° C. During regeneration, the hot air flows from the inlet of the catalyst bed to the outlet further heating the catalyst beds and removing coke that has deposited on the catalyst during the dehydrogenation step. The regeneration step provides heat to the catalyst bed, both by heat transfer from the air and by the combustion of the coke deposits on the catalyst. During the regeneration step, the heat-generating component may also generate additional heat, e.g., through the oxidation of the metal of the heat generating component to metal oxide. For example, in certain embodiments, the regeneration step increases the temperature of the first catalytic composition and, if present, the third catalytic composition by at least about 5° C., at least about 10° C., at least about 15° C., at least about 20° C., at least about 25° C., or even at least about 30° C. In certain embodiments, the regeneration step increases the temperature of the second catalytic composition by at least about 5° C., at least about 10° C., at least about 15° C., at least about 20° C., at least about 25° C., or even at least about 30° C. In certain such embodiments, the temperature increases are up to about 150° C., up to about 100° C., or up to about 50° C. The person of ordinary skill in the art will appreciate that conventional regeneration techniques can be used to prepare the catalyst bed for reduction at the beginning of each cycle.

Notably, however, as the reduction step also provides heat to the catalyst bed, the requirement for hot air in the regeneration step can be significantly reduced, and accordingly the processes can operate at lower air to hydrocarbon ratios, providing cost savings and added process efficiency.

As is conventional in dehydrogenation processes, the processes of the disclosure can be performed in a cyclic fashion. Thus, in certain embodiments, the processes as described herein further include repeating steps b) through step e) as described above at least once (e.g., at least three times, at least five times, at least 10 times, at least 100 times, at least 1000 times, or even at least 10,000 times, at least 20,000 times, or at least 40,000 times) on a particular load of catalyst The processes of the disclosure can in some embodiments be repeated up to 80,000 times between reloading catalysts.

The inventors have determined that, advantageously, the processes described herein can be operated at relatively low air/hydrocarbon ratios. Thus, the processes described herein can be performed with significantly lower energy costs per unit of dehydrogenated product produced. For example, in certain embodiments, the ratio of air in the regeneration step to total hydrocarbon feedstock is in the range of about 6.5 wt/wt to about 2 wt/wt. In one embodiment, the process as described above operates at the ratio of air in the regeneration step to hydrocarbon feedstock of in the range of about 6.5 wt/wt to about 3 wt/wt. In certain such embodiments, the ratio of air in the regeneration step to hydrocarbon is in the range of about 6 wt/wt to about 2 wt/wt, or in the range of about 6 wt/wt to about 3 wt/wt, about 6 wt/wt to about 3.2 wt/wt, or in the range of about 6 wt/wt to about 3.5 wt/wt, or in the range of about 5.8 wt/wt to about 3.7 wt/wt, or in the range of about 6 wt/wt to about 3.9 wt/wt, or in the range of about 5.8 wt/wt to about 3.9 wt/wt, or in the range of about 4.9 wt/wt to about 3.9 wt/wt, or in the range of about 4.5 wt/wt to about 3.5 wt/wt, or in the range of about 4.3 wt/wt to about 3.6 wt/wt, or in the range of about 4.0 wt/wt to about 3.8 wt/wt, or about 4.0 wt/wt, or about 3.9 wt/wt, or about 3.8 wt/wt.

The processes described herein can be performed at a variety of pressures and temperatures. The inventors have determined that, advantageously, the processes can be performed at pressures near atmospheric pressure, thereby reducing the energy costs per unit of dehydrogenated product produced. For example, in certain embodiments, the pressure of the step of contacting the hydrocarbon feedstock with the catalyst bed is in the range of about 0.1 atm to about 1.5 atm, or about 0.2 atm to about 1.5 atm, or about 0.3 atm to about 1.5 atm, or about 0.4 atm to about 1.5 atm, or about 0.5 atm to about 1.5 atm, or about 0.6 atm to about 1.5 atm, or about 0.7 atm to about 1.5 atm, or about 0.8 atm to about 1.5 atm, or about 0.9 atm to about 1.5 atm, about 0.1 atm to about 1 atm, or about 0.2 atm to about 1 atm, or about 0.3 atm to about 1 atm, or about 0.4 atm to about 1 atm, or about 0.5 atm to about 1 atm, or about 0.6 atm to about 1 atm, or about 0.7 atm to about 1 atm, or about 0.8 atm to about 1 atm, or about 1 atm to about 1.5 atm. For example, in other embodiments, the pressure of the step of contacting the hydrocarbon feedstock and the air with the catalyst bed is in the range of about 0.1 atm to about 1.3 atm, or about 0.2 atm to about 1.3 atm, or about 0.5 atm to about 1.3 atm, or about 0.7 atm to about 1.3 atm, or about 0.8 atm to about 1.2 atm, or about 0.7 atm to about 1.1 atm, or about 0.7 atm to about 1 atm, or about 0.8 atm to about 1.3 atm, about 0.8 atm to about 1.2 atm, about 0.8 atm to about 1.1 atm, or about 0.8 atm to about 1 atm. In other embodiments, the pressure of the step of contacting the hydrocarbon feedstock and the air with the catalyst bed is in the range of about 0.1 atm to about 1 atm, or about 0.2 atm to about 1 atm, or about 0.3 atm to about 1 atm, or about 0.3 atm to about 0.8 atm, or about 0.3 atm to about 0.7 atm, or about 0.4 atm to about 1 atm, or about 0.4 atm to about 0.7 atm, or about 0.4 atm to about 0.6 atm, or about 0.5 atm. In one particular embodiment, the pressure of the step of contacting the hydrocarbon feedstock and the air with the catalyst bed is about 1 atm.

In certain embodiments, the air and hydrocarbon feedstock are at inlet temperature of in the range of about 550° C. and about 720° C. In certain embodiments, the inlet temperature of hydrocarbon feedstock is in the range of about 580° C. to about 700° C., or in the range of about 580° C. to about 680° C., or in the range of about 580° C. to about 640° C., or in the range of about 580° C. to about 620° C., or in the range of about 600° C. to about 680° C., or in the range of about 620° C. to about 680° C., or in the range of about 620° C. to about 650° C., or in the range of about 600° C. to about 620° C., or in the range of about 600° C. to about 610° C., or about 600° C., or about 610° C., or about 620° C., or about 640° C., or about 660° C. In some other embodiments, the inlet temperature of air is in the range of about 600° C. to about 680° C., or in the range of about 620° C. to about 680° C., or in the range of about 620° C. to about 650° C., or in the range of about 600° C. to about 620° C., or in the range of about 600° C. to about 610° C., or about 600° C., or about 610° C., or about 620° C., or about 640° C., or about 660° C. Of course, the person of ordinary skill in the art will understand that in certain embodiments and applications, the temperatures and pressures may differ from those particularly described here.

The processes described herein can be performed at a variety of liquid hourly space velocities (LHSV). In some embodiments, reacting the hydrocarbon feedstock with the catalyst bed is at a liquid hourly space velocity in the range of about 0.5 hr$^{-1}$ to about 15 hr$^{-1}$. For example, in some embodiments, the liquid hourly space velocity is in the range of about 0.5 hr$^{-1}$ to about 10 hr$^{-1}$, about 0.5 hr$^{-1}$ to about 5 hr$^{-1}$, about 0.5 hr$^{-1}$ to about 3 hr$^{-1}$, about 0.7 hr$^{-1}$ to about 3 hr$^{-1}$, about 1 hr$^{-1}$ to about 3 hr$^{-1}$, or about 1 to about 2 hr$^{-1}$. In certain embodiments, the liquid hourly space velocity is in the range of about 1.2 hr$^{-1}$ to about 1.8 hr$^{-1}$. In other embodiments, the liquid hourly space velocity is in the range of about 1.3 hr$^{-1}$ to about 1.8 hr$^{-1}$, or in the range of about 1.4 hr$^{-1}$ to about 1.8 hr$^{-1}$, or in the range of about 1.5 hr$^{-1}$ to about 1.8 hr$^{-1}$, or in the range of about 1.6 hr$^{-1}$ to about 1.8 hr$^{-1}$, or in the range of about 1.7 hr$^{-1}$ to about 1.8 hr$^{-1}$. In one embodiment, the liquid hourly space velocity is about 1.8 hr$^{-1}$. Of course, the person of ordinary skill in the art will understand that in certain embodiments and applications, the hourly liquid space velocity values may differ from those particularly described here.

The person of ordinary skill in the art will appreciate that various hydrocarbons can be converted in the processes of the disclosure. For example, in certain embodiments, the hydrocarbon feedstock includes one or more (e.g., one) hydrocarbons selected from ethane, propane, butane, or iso-butane. In some embodiments, the hydrocarbon feedstock is propane.

In other embodiments, the hydrocarbon feedstock is iso-butane. In other embodiments, the hydrocarbon feedstock is paraffin.

EXAMPLES

The methods of the disclosure are illustrated further by the following examples, which are not to be construed as limiting the disclosure in scope or spirit to the specific procedures and in them.

Materials:

Catalyst 1:

A catalytic first component sold as CATOFIN® 300 catalyst (about 19 wt % chromium oxide based on total catalyst weight) and available from Clariant Corporation, Charlotte, N.C. is used in a commercial dehydrogenation unit for 180 days. The commercially-aged CATOFIN® 300 catalyst is then physically mixed with an inert, alpha-alumina, in a 57 vol % catalyst/43 vol % inert alpha-alumina.

Reactor Loading: 100 vol. % of CATOFIN® 300—alpha-alumina material is loaded.

Catalyst 2:

A heat-generating second component is prepared as provided in Example E (below). The commercially-aged CATOFIN® 300 catalyst is then physically mixed with the heat-generating second component in a 57 vol. % first component/43 vol. % heat-generating second component ratio to give Heat Generating Material (HGM).

Reactor Loading: approximately 33 vol. % of CATOFIN® 300—alpha-alumina mixture is loaded near the outlet of the down-flow adiabatic reactor, then approximately 33 vol. % of HGM/catalyst mixture is loaded into a middle section of the reactor, then approximately 33 vol. % of CATOFIN® 300—alpha-alumina mixture is loaded near the inlet.

Performance Testing:

Catalyst combinations are tested for the conversion of propane to propylene in a down-flow adiabatic reactor. Propane and air are fed into the reactor through an inlet and propylene is recovered from an outlet. The reactor is operated in the cyclic mode common for Houdry processes with the cycle times of 60 seconds for reduction by hydrogen, 540 seconds for dehydrogenation, 60 seconds for evacuation, 540 seconds for regeneration-reheat-oxidation, and 60 seconds for evacuation. The reactor is operated at atmospheric pressure during the regeneration step of the cycle. The cyclic operation is repeated 300 times.

Example 1 (Comparative)

Catalyst 1 (2382 g CATOFIN® 300/2200 cc α-Al₂O₃ inert) was used. The process conditions and results are shown in Table 1:

TABLE 1

| Process Conditions | | | | | |
|---|---|---|---|---|---|
| LHSV, h⁻¹ | 1.01 | 1.01 | 1.01 | 1.01 | 1.01 |
| Propane flow, g/hour | 1200 | 1200 | 1200 | 1200 | 1200 |
| Air to hydrocarbon ratio | 7.1 | 7.1 | 7.1 | 7.1 | 7.1 |
| Dehydrogenation pressure, atm | 0.5 | 0.5 | 0.5 | 0.5 | 0.5 |
| Air inlet temperature, ° C. | 540 | 560 | 580 | 600 | 600 |
| Hydrocarbon inlet temperature, ° C. | 540 | 560 | 580 | 600 | 620 |
| Performance | | | | | |
| Propane conversion, % | 17.96 | 22.73 | 27.1 | 31.6 | 37.6 |
| Propylene selectivity, % | 81.5 | 83.77 | 85.4 | 86.5 | 86.7 |
| Propylene yield, g/hour | 176 | 228 | 278 | 328 | 391 |

Example 2 (Comparative)

Catalyst 2 (2382 g CATOFIN® 300/1634 cc α-Al₂O₃ inert/564 g of HGM) was used. The process conditions and results are shown in Table 2:

TABLE 2

| Process Conditions | | | | | |
|---|---|---|---|---|---|
| LHSV, h⁻¹ | 1.01 | 1.01 | 1.01 | 1.01 | 1.01 |
| Propane flow, g/hour | 1200 | 1200 | 1200 | 1200 | 1200 |
| Air to hydrocarbon ratio | 7.1 | 7.1 | 7.1 | 7.1 | 7.1 |
| Dehydrogenation pressure, atm | 0.5 | 0.5 | 0.5 | 0.5 | 0.5 |
| Air inlet temperature, ° C. | 540 | 560 | 580 | 600 | 600 |
| Hydrocarbon inlet temperature, ° C. | 540 | 560 | 580 | 600 | 620 |
| Performance | | | | | |
| Propane conversion, % | 43.4 | 50.64 | 53.6 | 60.6 | 64.9 |
| Propylene selectivity, % | 87.5 | 87.4 | 87.2 | 86.2 | 83.5 |
| Propylene yield, g/hour | 456 | 531 | 561 | 627 | 650 |

Example 3

Catalyst 2 (2382 g CATOFIN® 300/1634 cc α-Al₂O₃ inert/564 g of HGM) was used. The process conditions and results are shown in Table 3:

TABLE 3

| Process Conditions | | | | |
|---|---|---|---|---|
| LHSV, h⁻¹ | 1.01 | 1.26 | 1.46 | 1.8 |
| Propane flow, g/hour | 1200 | 1512 | 1740 | 2160 |
| Air flow, L/hour | 8400 | 8400 | 8400 | 8400 |
| Dehydrogenation pressure, atm | 0.5 | 0.5 | 0.5 | 0.5 |
| Hydrocarbon inlet temperature, ° C. | 600 | 600 | 600 | 600 |
| Air inlet temperature, ° C. | 600 | 600 | 600 | 600 |
| Air to hydrocarbon ratio | 7.1 | 5.63 | 4.86 | 3.9 |
| Performance | | | | |
| Propane conversion, % | 59.1 | 52.5 | 46.9 | 40.3 |
| Propylene selectivity, % | 86.2 | 88.3 | 89.2 | 90.2 |
| Propylene yield, g/hour | 611 | 701 | 728 | 785 |

Example 4 (Comparative)

Catalyst 1 (2382 g CATOFIN® 300/2200 cc α-Al₂O₃ inert) was used. The process conditions and results are shown in Table 4:

TABLE 4

| Process Conditions | | | | |
|---|---|---|---|---|
| LHSV, h⁻¹ | 1.01 | 1.01 | 1.01 | 1.01 |
| Propane flow, g/hour | 1200 | 1200 | 1200 | 1200 |
| Air flow, L/hour | 8400 | 8400 | 8400 | 8400 |
| Air to hydrocarbon ratio | 7.1 | 7.1 | 7.1 | 7.1 |
| Dehydrogenation pressure, atm | 0.5 | 0.5 | 0.5 | 0.5 |
| Hydrocarbon inlet temperature, ° C. | 600 | 600 | 600 | 600 |
| Air inlet temperature, ° C. | 600 | 620 | 640 | 660 |
| Performance | | | | |
| Propane conversion, % | 31.6 | 37.6 | 42.6 | 49.2 |
| Propylene selectivity, % | 86.5 | 86.7 | 86.9 | 86.2 |
| Propylene yield, g/hour | 328 | 391 | 444 | 509 |

Example 5

Catalyst 2 (2382 g CATOFIN® 300/1634 cc α-Al₂O₃ inert/564 g of HGM) was used. The process conditions and results are shown in Table 5:

TABLE 5

| Process Conditions | | | | |
|---|---|---|---|---|
| LHSV, h⁻¹ | 1.8 | 1.8 | 1.8 | 1.8 |
| Propane flow, g/hour | 2160 | 2160 | 2160 | 2160 |
| Air flow, L/hour | 8400 | 8400 | 8400 | 8400 |
| Air to hydrocarbon ratio | 3.9 | 3.9 | 3.9 | 3.9 |
| Dehydrogenation pressure, atm | 0.5 | 0.5 | 0.5 | 0.5 |
| Hydrocarbon inlet temperature, ° C. | 600 | 600 | 600 | 600 |
| Air inlet temperature, ° C. | 600 | 620 | 640 | 660 |
| Performance | | | | |
| Propane conversion, % | 40.3 | 42.5 | 45.7 | 48.5 |
| Propylene selectivity, % | 90.2 | 90.2 | 90 | 89.3 |
| Propylene yield, g/hour | 785 | 828 | 888 | 936 |

Example 6

Catalyst 2 (2382 g CATOFIN® 300/1634 cc α-Al₂O₃ inert/564 g of HGM) was used. The process conditions and results are shown in Table 6:

TABLE 6

| Process Conditions | | | | |
|---|---|---|---|---|
| LHSV, h$^{-1}$ | 1.8 | 1.8 | 1.8 | 1.8 |
| Propane flow, g/hour | 2160 | 2160 | 2160 | 2160 |
| Air flow, L/hour | 8400 | 8400 | 8400 | 8400 |
| Air to hydrocarbon ratio | 3.9 | 3.9 | 3.9 | 3.9 |
| Dehydrogenation pressure, atm | 1 | 1 | 1 | 1 |
| Air inlet temperature, ° C. | 600 | 600 | 600 | 600 |
| Hydrocarbon inlet temperature, ° C. | 620 | 640 | 660 | 680 |
| Performance | | | | |
| Propane conversion, % | 41.7 | 44.2 | 47.9 | 50.7 |
| Propylene selectivity, % | 88 | 87.7 | 86.4 | 85.9 |
| Propylene yield, g/hour | 793 | 837 | 894 | 941 |

Additional Material Preparations

A variety of preparations of additional materials that may be useful in practicing the present invention are provided below.

Example A

A catalytic component sold under the trade name Catofin® 300 catalyst and available from Clariant Corporation is used in a commercial dehydrogenation unit for 180 days. The catalyst has a chromium oxide concentration of about 19 wt % based on total catalyst weight.

Example B

A chromia/potassium oxide/gamma-alumina dehydrogenation catalyst having a mean particle size of about 75 μm is prepared. The catalyst has a chromium oxide concentration of 17.5 wt % and a potassium oxide concentration of 1.0 wt % based on total catalyst weight.

Example C

A heat-generating component is prepared as follows: an alpha-alumina support is impregnated with a saturated solution of copper nitrate, the impregnated support is then dried at 120° C. followed by calcining at 750° C. in an air-steam atmosphere. The heat-generating component has a CuO concentration of about 11 wt % based on the weight of the heat-generating component.

Example D

A heat-generating component is prepared as follows: calcium-aluminate (Ca-aluminate) is pelletized as approximately 3.5 mm pellets, the Ca-aluminate is then calcined at about 1300° C. for about 10 hours, the calcined material is then impregnated with a saturated solution of copper nitrate and manganese nitrate, and the impregnated material is dried for about 4 hours at about 250° C. followed by calcining at from about 500° C. for about 5 hours. The heat-generating second component has a CuO concentration of about 11 wt % and a MnO$_2$ concentration of about 0.5 wt % based on the weight of the heat-generating component.

Example E

A heat-generating component is prepared as follows: boehmite alumina is mixed with calcium oxide and the mixture is spherudized to make 6 mm diameter pellets which are dried at 120° C. and then calcined at 1300° C., the pellets having a final CaO content of 18 wt %. The calcined pelletized material is impregnated with a saturated solution of copper nitrate and manganese nitrate, and the impregnated material is dried at about 250° C. followed by calcining in air at 1400° C. The heat-generating component has a CuO concentration of about 11 wt and a MnO$_2$ concentration of about 0.5 wt % based on the weight of the heat-generating component.

Example F

A heat-generating component is prepared as follows: alumina trihydrate (gibbsite) is pelletized as approximately 5 mm pellets, the gibbsite is then calcined at about 550° C. for about 4 hours, the calcined material is then impregnated with a saturated solution of copper nitrate, and the impregnated material is dried for about 4 hours at about 250° C. followed by calcining at from about 500° C. to 1400° C. The heat-generating component has a CuO concentration of about 11 wt % and a MnO$_2$ concentration of about 0.5 wt % based on the weight of the heat-generating component.

Example G

A heat-generating component is prepared according to the invention as follows: a gamma-alumina support having a mean particle size of about 75 μm is impregnated with a saturated solution of copper nitrate and manganese nitrate, the impregnated material is then dried at about 250° C. followed by calcining in air at 750° C. The heat-generating component has a CuO concentration of about 8 wt % and a MnO$_2$ concentration of about 0.4 wt % based on the weight of the heat-generating component.

Example H

The catalytic component of Example A is physically mixed with an inert component, alpha-alumina, in a 55 vol. % first component/45 vol. % alpha-alumina ratio.

Example I

The catalytic component of Example A is physically mixed with the heat-generating component of Example E in a 55 vol. % catalytic component/45 vol. % heat-generating component ratio.

Example J

The catalytic component of Example B is physically mixed with the heat-generating component of Example G in an 80 vol. % catalytic component/20 vol. % heat-generating component ratio.

Example K

The catalytic component of fresh Catofin® 300 catalyst is physically mixed with the heat-generating component of Example F in a 55 vol. % first component/45 vol. % heat-generating component ratio.

Example L

The catalytic component of fresh Catofin® 300 catalyst is impregnated with a saturated solution of copper nitrate, and the copper-impregnated chromium-based catalyst is dried at 120° C. and calcined at 750° C. in an air-steam atmosphere. The copper-impregnated catalyst has a chromium oxide concentration of 17.5 wt % and a copper oxide concentration of 11 wt % based on total catalyst weight.

Example M

A catalytic component is prepared according to Example 1 of WO 02/068119, which is hereby incorporated herein by reference in its entirety. The catalyst is prepared by combining 860 g boehmite alumina, 800 g copper hydroxide carbonate, 120 g barium acetate, 100 g $CrO_3$, 700 g $NH_4HCO_3$, and 250 g deionized water in an Eirich mixer. Particles approximately 3 mm in diameter are formed and dried at 120° C. for 8 hours and calcined in oven at 650° C. for 10 hours. The copper-impregnated catalyst has a chromium oxide concentration of 45 wt % and a copper oxide concentration of 40 wt % based on total catalyst weight.

Example N

A prior art catalyst is prepared according to Example 1 of U.S. Pat. No. 5,108,973, which is hereby incorporated herein by reference in its entirety. The catalyst is prepared by blending 763.8 g of alumina sol (containing 7.51% $Al_2O_3$) and 89.3 g of chromium nitrate hexahydrate in a one-gallon blender until the solids are dissolved. Copper nitrate hexahydrate (116.3 g) is dissolved in 200 mL DI water and added to the blender. Then 61.8 mol of boric acid is dissolved in 350 mL warm deionized water and also added to the blender. The mixture is blended for an additional two minutes until the mixture becomes homogeneous and a deep blue color. Then 700 ml of 20% ammonium hydroxide in methanol solution is added to form a thick gel. The gel is placed on plastic trays for drying and is dried for 4 hour at 180° C., and then calcined by the following sequence: 25° C. for 2 hours, 175° C. for 12 hours, 400° C. for 4 hours, 830° C. for 8 hours, 830° C. for 4 hours, 250° C. for 3 hour and then cooled to RT. The calcined material is tabletted to form particles of 3 mm diameter. The copper-impregnated catalyst has a chromium oxide concentration of 19 wt % and a copper oxide concentration of 25 wt % based on total catalyst weight.

COMPARATIVE EXAMPLES

The following comparative examples provide the person of ordinary skill in the art additional guidance in practicing the processes described herein.

Examples O and P

Catalyst combinations are tested for the conversion of propane to propylene in a down-flow adiabatic reactor having a catalyst bed volume of approximately 3600 cc. Propane is fed into the reactor through an inlet and propylene is recovered from an outlet. The process is carried out at a liquid hourly space velocity of 1.0, with propane temperatures from 540° C. to 600° C. and air temperatures from 540° C. to 620° C., and at an air to hydrocarbon ratio of 7.1 wt/wt. The reactor is operated in the cyclic mode common for Houdry processes with the cycle times of 60 seconds for reduction by hydrogen, 540 seconds for dehydrogenation, 60 seconds for evacuation, 540 seconds for regeneration-reheat-oxidation, and 60 seconds for evacuation. The reactor is operated at a pressure of 0.5 atm during the dehydrogenation step of the cycle and at atmospheric pressure during the regeneration step of the cycle. The cyclic operation is repeated 300 times.

Example O

Reactor Loading—100 vol. % catalyst combination of Example H.

Example P

Reactor Loading—approximately 35 vol. % of material from Example H is loaded near the outlet of the down-flow adiabatic reactor, then approximately 30 vol. % of material from Example I is loaded into a middle section of the reactor, then approximately 35 vol. % of material from Example H is loaded near the inlet.

TABLE 7

Performance characteristics of catalysts in propane dehydrogenation (Adiabatic Fixed Bed Reactor)

|  | Example O | Example P |
|---|---|---|
| Bed Components (vol %) | 100% Ex. H | 35% Ex. H/30% Ex. I/ 35% Ex. H |
| Heat-Generating Component | none | copper oxide/ manganese oxide/ Ca-aluminate |
| Inlet Propane T = 540° C. | | |
| Propane Conversion: [wt %] | 18.3 | 45.1 |
| Propane Selectivity: [wt %] | 83.3 | 87.0 |
| Average Bed Temp (° C.) | 523.5 | 551.2 |
| Inlet Propane T = 560° C. | | |
| Propane Conversion: [wt %] | 22.3 | 50.5 |
| Propane Selectivity: [wt %] | 83.8 | 87.0 |
| Average Bed Temp (° C.) | 534.3 | 561.4 |
| Inlet Propane T = 580° C. | | |
| Propane Conversion: [wt %] | 27.4 | 54.5 |
| Propane Selectivity: [wt %] | 86.7 | 87.4 |
| Average Bed Temp (° C.) | 541.9 | 572.9 |
| Inlet Propane T = 600° C. | | |
| Propane Conversion: [wt %] | 31.8 | 60.1 |
| Propane Selectivity: [wt %] | 86.3 | 85.3 |
| Average Bed Temp (° C.) | 550.0 | 579.8 |
| Temperature Profile | FIG. 1 | FIG. 2 |

Examples Q and R

Catalyst combinations are tested for the conversion of isobutane to isobutylene in a pseudo-adiabatic fluid bed reactor having a catalyst bed volume of approximately 75 cc. Isobutane and air are fed into the reactor through an inlet and isobutylene is recovered from an outlet. The process is carried out at a liquid hourly space velocity of –3.34, with isobutane and air temperatures from 550° C. to 590° C., and at an air to hydrocarbon ratio of 3.5 wt/wt. The reactor is operated in the cyclic mode with the cycle times of 60 seconds for reduction by hydrogen, 540 seconds for dehydrogenation, 60 seconds for nitrogen purge, 540 seconds for oxidation, and 60 seconds for nitrogen purge. The reactor is operated at atmospheric pressure during both the dehydrogenation and regeneration steps of the cycle. The cyclic operation is repeated 30 times.

Example Q

Reactor Loading—100 vol. % catalyst combination of Example B.

Example R

Reactor Loading—100 vol. % catalyst combination of Example J.

TABLE 8

Performance characteristics of catalysts in isobutane
dehydrogenation (Pseudo-adiabatic Fluid Bed Reactor)

|  | Example Q | Example R |
|---|---|---|
| Components (vol %) | 100% Ex. B | 100% Ex. J |
| Heat-Generating Component | none | copper oxide/ manganese oxide/ gamma-alumina |
| Inlet Isobutane T = 550° C. | | |
| Isobutane Conversion: [wt %] | 34.2 | 42.6 |
| Isobutane Selectivity: [wt %] | 89.5 | 91.2 |
| Inlet Isobutane T = 570° C. | | |
| Isobutane Conversion: [wt %] | 40.1 | 46.7 |
| Isobutane Selectivity: [wt %] | 86.6 | 90.3 |
| Inlet Isobutane T = 590° C. | | |
| Isobutane Conversion: [wt %] | 47.0 | 53.2 |
| Isobutane Selectivity: [wt %] | 84.8 | 87.5 |

Examples S-V

Catalyst combinations are tested in an isothermal fixed bed reactor having a catalyst bed volume of approximately 30 cc for the conversion of isobutane to isobutylene. Isobutane and air are fed into the reactor through an inlet and isobutylene is recovered from an outlet. The dehydrogenation reaction is conducted at temperatures of 537° C., 567° C. and 593° C. and at a liquid hourly space velocity (LHSV) of ~2/hr.

Example S

Reactor Loading—100 vol. % catalyst combination of Example K.

Example T

Reactor Loading—100 vol. % catalyst combination of Example L.

Example U

Reactor Loading—100 vol. % catalyst combination of Example M.

Example V

Reactor Loading—100 vol. % catalyst combination of Example N.

TABLE 9

Performance characteristics of catalysts in isobutane
dehydrogenation (Isothermal Fixed Bed Reactor)

|  | Example S | Example T | Example U | Example V |
|---|---|---|---|---|
| Components (vol %) | Example K | Example L | Example M | Example N |
| Heat-Generating Component | copper oxide/ α-alumina | none | none | none |
| Reaction T = 537° C. | | | | |
| Isobutane Conversion: [wt %] | 55.1 | 17.9 | 1.9 | 7.7 |
| Isobutylene Selectivity: [wt %] | 92.3 | 89.2 | 33.9 | 55.7 |
| Isobutylene Yield: [wt %] | 50.9 | 15.9 | 0.6 | 4.0 |
| Reaction T = 567° C. | | | | |
| Isobutane Conversion: [wt %] | 64.8 | 23.4 | 2.1 | 9.8 |
| Isobutylene Selectivity: [wt %] | 88.2 | 86.7 | 29.2 | 52.6 |
| Isobutylene Yield: [wt %] | 57.2 | 20.3 | 0.6 | 5.2 |
| Reaction T = 593° C. | | | | |
| Isobutane Conversion: [wt %] | 77.3 | 32.8 | 3.5 | 15.7 |
| Isobutylene Selectivity: [wt %] | 81.5 | 81.1 | 30.6 | 47.3 |
| Isobutylene Yield: [wt %] | 63.0 | 26.5 | 1.1 | 7.4 |

Figure 2:
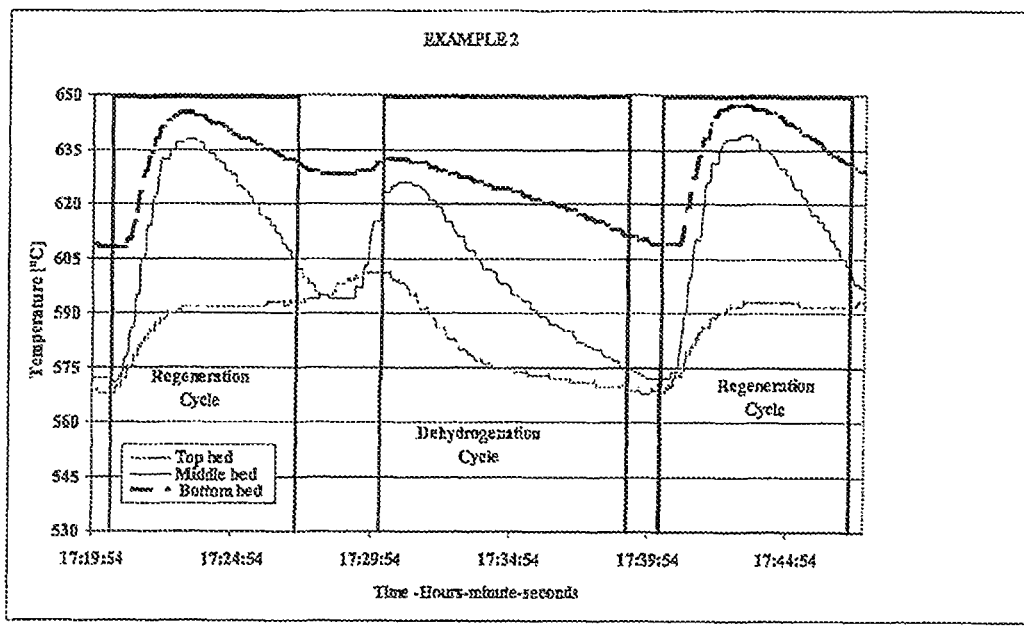

FIGS. 1 and 2 show the temperature profiles in the catalyst bed for Examples O and P, respectively. As demonstrated by the figures, when the heat-generating component is included within the fixed catalyst bed during a Houdry dehydrogenation process, the catalyst bed temperature is more consistent throughout the entire bed. Without the heat-generating component, the fluctuation in the temperature at the inlet section covers a range of about 75° C. while the fluctuation in the temperature at the outlet section covers a range of only about 5° C. Moreover, the temperature at the outlet section of the bed remains at about 560° C.—a temperature lower than desired to have optimal conversion performance from the catalyst. With the heat-generating component, both the inlet and outlet sections of the bed experience temperature fluctuations over the course of the cyclic process of about 45° C., but the average temperature at the inlet section is about 580° C. whereas the average temperature at the outlet section is about 625° C., providing greater efficiency overall for the catalyst. As shown in Table 7, this translates to significantly higher conversion without sacrificing selectivity.

Similarly, as shown in Table 8, improvement in conversion rate is also seen when the heat-generating second component is used in fluid bed systems. Although the increase in conversion rate is not as significant in the fluid bed application as in the fixed bed application, the fluid bed application does demonstrate a directional increase in selectivity in addition to the increase in conversion indicating that the overall process is more efficient than the prior art catalyst bed that does not include a heat-generating component.

Surprisingly, as shown by the results in Table 9, when copper is combined with chromium in a dehydrogenation catalyst composition (Ex. T), the conversion and yield from the dehydrogenation process in an isothermal unit is significantly lower than when copper is present in the catalyst bed as a component separate from but physically mixed with the chromium oxide dehydrogenation catalyst (Ex. S). Using higher concentrations of chromium oxide and/or copper oxide (Ex. U and V) does not alter these overall findings.

It is anticipated that the improved cyclic, endothermic hydrocarbon conversion processes taught herein may be used in any process involving endothermic reactions where temperature control within the catalyst bed is desired. Such processes include, but are not limited to, fixed bed paraffin dehydrogenation. In these processes, the catalyst and the catalyst combined with the heat-generating material may be layered or homogeneously mixed. Similarly, it is anticipated that the combinations of a reaction-specific catalyst combined with a heat-generating second component may be used in any process where temperature control within the catalyst bed is desired. It is understood that the composition of the catalyst and the specific processing conditions may be varied without exceeding the scope of this invention.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:

1. A process for dehydrogenation of, the process comprising:
   a) providing a reactor having a fixed catalyst bed, the fixed catalyst bed having an inlet section, a middle section and optionally an outlet section, wherein
      the inlet section of the fixed catalyst bed has a first catalyst composition disposed therein, the first catalyst composition comprising a dehydrogenation catalytic component optionally physically mixed with an inert component,
      the middle section of the fixed catalyst bed has a second catalyst composition disposed therein, the second catalyst composition comprising a dehydrogenation catalytic component physically mixed with a heat-generating component, and
      the outlet section, if present, of the fixed catalyst bed having a third catalyst composition disposed therein, the third catalyst composition comprising a dehydrogenation catalytic component optionally physically mixed with an inert component,
      wherein the middle section of the fixed catalyst bed is in thermal communication with the inlet section of the fixed catalyst bed and, if present, the outlet section of the fixed catalyst bed;
   b) reducing the fixed catalyst bed wherein the heat-generating component of the second catalytic composition generates heat that passes into the first catalyst composition and, if present, the third catalytic composition; then
   c) contacting the propane with the fixed catalyst bed to form propylene; then
   d) optionally, purging the fixed catalyst bed; and
   e) regenerating the fixed catalyst bed by contacting the fixed catalyst bed with air, wherein a ratio of air in the regenerating step to the propane in the contacting step is in a range of about 6.5 wt/wt to about 2 wt/wt.

2. The process of claim 1, wherein the ratio of air in the regenerating step to the propane is in a range of about 5.8 wt/wt to about 3.7 wt/wt.

3. The process of claim 1, wherein a pressure of the step of contacting the propane with the fixed catalyst bed is in a range of about 0.9 atm to about 1.5 atm.

4. The process of claim 1, wherein a pressure of the step of contacting the propane with the fixed catalyst bed is in a range of about 0.1 atm to about 1.5 atm.

5. The process of claim 1, wherein the air and the propane are at inlet temperature in a range of about 550° C. and about 720° C.

6. The process of claim 1, wherein the step of contacting the propane with the fixed catalyst bed is at a liquid hourly space velocity in a range of about 0.5 hr$^{-1}$ and about 15 hr$^{-1}$.

7. The process of claim 1, wherein the heat generated by the heat-generating component is less than the amount of heat consumed by the dehydrogenation of the propane.

8. The process of claim 1, wherein the dehydrogenation catalytic component of each of the first, second and, if present, third catalyst compositions comprises, disposed on an alumina support, chromium oxide in an amount in a range of about 15 to about 25 wt %, and, optionally, potassium oxide in an amount up to about 5 wt %.

9. The process of claim 1, wherein the dehydrogenation catalytic component of each of the first, second and, if present, third catalyst compositions comprises, disposed on an alumina support, from about 17 wt % to about 22 wt % $Cr_2O_3$.

10. The process of claim 1, wherein the heat-generating component comprises a metal in oxide form selected from the group consisting of copper, chromium, molybdenum, vanadium, cerium, yttrium, scandium, tungsten, manganese, iron, cobalt, nickel, silver, bismuth and combinations thereof, supported on a carrier.

11. The process of claim 10, the metal in oxide form is provided at a concentration of about 2 wt % to about 40 wt % of the total heat-generating component weight.

12. The process of claim 10, wherein the carrier is selected from the group consisting of aluminum oxides, aluminum hydroxides, aluminum trihydroxide, boehmite, pseudo-boehmite, gibbsite, bayerite, transition aluminas, alpha-alumina, gamma-alumina, silica/alumina, silica, silicates, aluminates, calcium aluminate, barium hexaluminate, calcined hydrotalcites, zeolites, zinc oxide, chromium oxides, magnesium oxides and combinations thereof.

13. The process of claim 1, wherein the heat generating component comprises, disposed on a carrier, copper oxide in an amount in a range of about 3 wt % to about 20 wt %; and, optionally, manganese oxide in an amount up to about 5 wt %.

14. The process of claim 1, wherein reducing the fixed catalyst bed comprises treatment of the fixed catalyst bed with hydrogen.

15. The process of claim 1, wherein the reducing step increases the temperature of the first catalyst composition by at least about 15° C., as compared to the temperature of the first catalyst composition before the reducing step.

16. The process of claim 1, wherein the heat-generating component is substantially inactive to catalyze the dehydrogenation of the propane.

17. The process of claim 1, further comprising:
   f) repeating step b) through step e) at least five times.

18. The process of claim 1, wherein the outlet section of the fixed catalyst bed is present.

19. The process of claim 1, wherein
   the ratio of air in the regenerating step to the propane is in a range of about 5.8 wt/wt to about 3.7 wt/wt;
   the air and the propane are at inlet temperature in a range of about 550° C. and about 720° C.;
   the dehydrogenation catalytic component of each of the first, second and, if present, third catalyst compositions comprises, disposed on an alumina support, chromium oxide in an amount in the range of about 15 to about 25 wt %, and, optionally, potassium oxide in an amount up to about 5 wt %; and the heat generating component comprises, disposed on a carrier, copper oxide in an amount in the range of about 3 wt % to about 20 wt %; and, optionally, manganese oxide in an amount up to about 5 wt %.

* * * * *